US006046358A

United States Patent [19]
Berris et al.

[11] Patent Number: 6,046,358
[45] Date of Patent: Apr. 4, 2000

[54] CATALYSIS IN HALOGEN EXCHANGE REACTIONS

[75] Inventors: Bruce C. Berris; Chi-Hung Cheng, both of Baton Rouge, La.

[73] Assignee: Albemarle Corporation, Richmond, Va.

[21] Appl. No.: 09/351,888

[22] Filed: Jul. 13, 1999

Related U.S. Application Data

[62] Division of application No. 08/975,924, Nov. 21, 1997, Pat. No. 5,965,781.

[51] Int. Cl.⁷ ........................................................ C07F 9/02
[52] U.S. Cl. ................................................................ 564/12
[58] Field of Search ................................................. 564/12

[56] References Cited

U.S. PATENT DOCUMENTS

| | | |
|---|---|---|
| 3,064,058 | 11/1962 | Duesel et al. . |
| 3,231,625 | 1/1966 | Nyman . |
| 3,240,824 | 3/1966 | Boudakian et al. . |
| 3,277,192 | 10/1966 | Fielding et al. . |
| 3,280,124 | 10/1966 | Boudakian et al. . |
| 3,296,269 | 1/1967 | Boudakian et al. . |
| 3,300,537 | 1/1967 | Bennett et al. . |
| 3,303,197 | 2/1967 | Haszeldine et al. . |
| 3,312,746 | 4/1967 | Fielding . |
| 3,314,955 | 4/1967 | Boudakian et al. . |
| 3,334,150 | 8/1967 | Pierce et al. . |
| 3,388,174 | 6/1968 | Fielding et al. . |
| 3,408,412 | 10/1968 | Blackley et al. . |
| 3,429,935 | 2/1969 | Wall et al. . |
| 3,453,337 | 7/1969 | Bennett et al. . |
| 3,485,839 | 12/1969 | Fuller . |
| 3,574,775 | 4/1971 | Fuller . |
| 3,852,365 | 12/1974 | Maher . |
| 4,069,262 | 1/1978 | Kunz . |
| 4,174,349 | 11/1979 | Evans et al. . |
| 4,209,457 | 6/1980 | Fuller . |
| 4,226,811 | 10/1980 | Oeser et al. . |
| 4,229,365 | 10/1980 | Oeser et al. . |
| 4,287,374 | 9/1981 | North . |
| 4,543,217 | 9/1985 | Erpenbach et al. . |
| 4,684,734 | 8/1987 | Kaieda et al. . |
| 4,937,397 | 6/1990 | Pews et al. . |
| 4,978,769 | 12/1990 | Kysela et al. . |
| 5,315,043 | 5/1994 | Fernandez et al. . |
| 5,476,976 | 12/1995 | Schach et al. . |
| 5,789,631 | 8/1998 | Balhoff et al. . |
| 5,824,827 | 10/1998 | Bildinov et al. . |

FOREIGN PATENT DOCUMENTS

| | | |
|---|---|---|
| 0003344 | 8/1979 | European Pat. Off. . |
| 0678864 | 4/1994 | U.S.S.R. . |
| 0755668 | 8/1956 | United Kingdom . |
| 0866810 | 5/1961 | United Kingdom . |
| 0970746 | 9/1964 | United Kingdom . |
| 0996498 | 6/1965 | United Kingdom . |
| 1004375 | 9/1965 | United Kingdom . |
| 1026290 | 4/1966 | United Kingdom . |
| 1071323 | 6/1967 | United Kingdom . |
| 1256082 | 12/1971 | United Kingdom . |
| 1340421 | 12/1973 | United Kingdom . |
| 1360327 | 7/1974 | United Kingdom . |
| 9200270 | 1/1992 | WIPO . |

OTHER PUBLICATIONS

"Dimethyl Sulphone as a Reaction Solvent for the Preparation of Aromatic Fluorides"; By L. D. Starr et al; Chemistry and Industry Jul. 21, (1962); pp. 1328–1329.

"No. 163 Preparation de derives perhalogenes aromatiques polyfluores par reaction d'echange d'halogene, utilisant une phase sel fondu"; By: J. Hitzke et al; Bulletin de la Societe Chimique De France (1974); No. 5–6; pp. 811–814.

"La Fluoration De L'Hexachlorobenzene Et De LA Pentachloropyridine En Milieu De Fluorure De Potassium Solide"; By: J. Hitzke; Journal of Fluorine Chemistry (1980); vol. 16, pp. 103–128.

"Hlaex fluorination of 1,2,4,5–tetrachlorobenzene in a pressure reactor"; By: Yoshikazu Kimura et al, (1992); Journal of Fluorine Chemistry, vol. 59, pp. 289–291.

Tetraphenylphosphonium bromide–catalyzed 'Halex' fluorination of chloroaryl sulfonyl chlorides; By: Suzuki et al., Journal of Fluorine Chemistry, (1991); vol. 55, pp. 335–337.

"Halex Fluorination of Chlorinated Benzaldehydes and Benzoyl Chlorides"; By: R. Eric Banks et al., Journal of Fluorine Chemistry (1990); vol. 46, pp. 529–537.

La Fluoration par kf de Perhalogenes Organiques Aromatiques en Presence de Faibles Quantites de Sulfolane ou D'Eau. Spectres de Masses des Melanges Obtenus en Serie Benzenique; By: J. Hitzke; Journal of Fluorine Chemistry (1981); vol. 18, pp. 101–115.

Lundin, et al., "Investigation of Methods of Preparing Polyfluoroaromatic Compounds", Trudy Instituta Khimii, vol. 16, 1968, pp. 67–73, translated pp. 1–14.

Vorozhtsov, et al., "Formation of Chloroheptafluorotoluenes in the Reaction of Hexachlorobenzene With Potassium Flouride", Zhurnal Vsesoyuznoe Khimicheskoe Obschestvo im. D. I. Medeleeva, vol. 14(1), 1969, p. 114. Translated pp. 1–2.

Aromatic Fluorine Compounds. VII. Replacement of Aromatic–Cl and –NO 2 Groups by –F 1,2; By: G. C. Finger et al., (1956); Contributed from the Illinois State Geological Survey; vol. 78, pp. 6034–6036.

(List continued on next page.)

*Primary Examiner*—Alan Siegel
*Attorney, Agent, or Firm*—Philip M. Pippenger

[57] ABSTRACT

Impure tetra(dihydrocarbylamino)phosphonium halide is contacted with a liquid cyclic ether to dissolve the phosphonium halide and leave at least a portion of the impurities comprising at least quaternary ammonium halide or an amidophosphoxide remaining in the solid state. The solids and the liquid phase are separated from each other, an anhydrous non-solvent for the tetra(dihydrocarbylamino) phosphonium halide is mixed with the separated liquid phase to precipitate the tetra(dihydrocarbylamino) phosphonium halide, which is then separated from the liquid phase. The so-treated tetra(dihydrocarbylamino) phosphonium halide is more efficient as a catalyst for halogen exchange reactions than the original untreated tetra(dihydrocarbylamino)phosphonium halide.

7 Claims, 1 Drawing Sheet

OTHER PUBLICATIONS

Aromatic fluoro derivatives. VIII. Reaction of chloronitro compounds with fluorides of alkali metals; Chemical Abstract, v.57,(1962) cols. h 9706–b 9707.

"Interaction of Chloroaromatic Compounds with Alkali Metal Fluorides in the Presence of Crown–Ethers"; Aksenov, et al., Journal of Fluorine Chemistry; vol. 28 (1985), pp. 73–87.

Heterocyclic Polyfluoro–compounds. Part VI. Preparation of Pentafluoropyridine and Chlorofluoropyridines from Pentachloropyridine; By: R. E. Banks, et al; J. Chem. Soc., 1965; pp. 594–597.

"Preparation of Polyfluoroaromatic Compounds by the Reaction of Perhalogeno–aromatic Compounds with Potassium Fluoride in Sulpholan"; By: G. Fuller; Journal Chemical Society, (1965); pp. 6264–6267.

Solvent–free Fluorination of Partially–chlorinated Heterocyclics: Synthesis of 2,6–Difluoropyridine from 2,6 Dichloropyridine; By: Boudakian, et al., J. Heterocyclic Chem., vol. 5, (1968); pp. 683–684.

"Aromatic Nucleophilic Substitution Reactions"; Chem. Reviews; American Society; vol. 48 (1951); pp. 273–277 and p. 405.

"Polyfluoro–heterocyclic Compounds. Part I. The Preparation of Fluoro–, Chlorofluoro–, and Chlorofluorohydro–pyridines"; By: R. D. Chambers, et al; J. Chemical Society (1964); pp. 3573–3576.

"Aromatic Fluorine Compounds. XI. Replacement of Chlorine by Fluorine in Halopyridines"; G. C. Finger, et al; Journal of Org. Chemical (1963); vol. 28, 1963, pp. 1666–1668.

"Aromatic Fluorine Compounds. VIII. Plant Growth Regulators and Intermediates"; By: G. C. Finger, et al; Journal of American Chemical Society (1959); vol. 81, pp. 94–101.

"Some Properties of Phosphorimidic Triamides", by Koidan et al., Institute of Organic Chemistry, Academy of Sciences of the Ukraninian SSR. Translated from Zhurnal Obshchei Khimii, vol. 52, No. 9, pp. 2001–2011, Sep. 1982. Translated pp. 1779–1787.

"The Replacement of Chlorine by Fluorine in Organic Compounds"; By Hans Gottlieb; Journal American Chemical Society (1936); vol. 58, pp. 532–533.

Preparation of 3–Fluorophthalic Anhydride; By: Adam Heller; J. Org. Chem. (1960); vol. 25, pp. 834–835.

"Fluorination of Perhalobenzenes with Potassium Fluoride in Polar Solvents"; By: G. W. Holbrook, et al; J. Org. Chem. (1966), vol. 31, pp. 1259–1261.

The Synthesis of Highly Fluorinated Compounds by Use of Potassium Fluoride in Polar Solvents; By: John T. Maynard; J. Org. Chem. (1963); vol. 28, pp. 112–115.

The Synthesis of Pentafluorobenzoic Acid and a New Purification of Chloropentafluorobenzene; By D. E. Pearson et al.; Georg Thieme Publishers (1978); p. 127.

The Chemistry of 'Naked' Anions. I. Reactions of the 18–Crown–6 Complex of Potassium Fluoride with Organic Substrates in Aprotic Organic Solvents1; Journal of the Amiercan Chemical Soc.; vol. 96(7), (1974) p. 2250–2252.

Polyfluoroarenes. Part XVI. A Convenient Synthesis of Pentafluorobenzonitrile; By: J. M. Birchall et al.; Journal Chemistry Society (1971); pp. 1341–1342.

"Inexpensive, Active KF for Nucleophilic Aromatic Displacement Reactions", Tetrahedron, vol. 51, No. 22, 1995, pp. 6363–6376, Smyth et al.

CATALYSIS IN HALOGEN EXCHANGE REACTIONS

REFERENCE TO RELATED APPLICATION

This is a Division of U.S. application Ser. No. 08/975,924, filed Nov. 21, 1997, now U.S. Pat. No. 5,965,781, issued Oct. 12, 1999.

REFERENCE TO OTHER APPLICATIONS

Reference is invited to the following co-pending applications: U. S. application Ser. No. 08/754,338, filed Nov. 22, 1996, now commonly owned by the same assignee as the present application, and issued as U.S. Pat. No. 5,824,827 on Oct. 20, 1998; and U.S. applications Ser. Nos. 08/756,103, now abandoned; 08/756,104, now U.S. Pat. No. 5,789,631 issued Aug. 4, 1998; and Ser. No. 08/756,107, now abandoned, each filed Nov. 25, 1996, and each of which is commonly owned by the same assignee as the present application.

TECHNICAL FIELD

This invention relates to improved halogen exchange reactions involving haloaromatic compounds and alkali metal fluorides, and more particularly to improved catalysts and catalytic processes for producing polyfluorinated aromatics by catalyzed halogen exchange reactions.

BACKGROUND

Halogen exchange reactions for fluorinating haloaromatic compounds using alkali metal fluorides have been extensively studied heretofore. Typically they involve the reaction of a chloroaromatic compound with potassium fluoride, rubidium fluoride or cesium fluoride by heating the reactants to extremely high temperatures (above about 400° C.) in the absence of an ancillary diluent or solvent, or by conducting the reaction at temperatures of around 200–230° C. in an aprotic solvent such as sulfolane. It has also been reported that organic fluorine compounds such as pentafluorobenzonitrile, tetrafluorophthalonitriles and pentafluoropyridine can be formed by reacting a corresponding chloro- or bromo-substituted compound with alkali metal halide such as potassium fluoride in benzonitrile as solvent at 190° C. to 400° C. in a sealed autoclave under autogenous pressure.

Use of catalysts in some exchange reactions has also been studied. Such catalysts have included quaternary ammonium salts, metal carbonyls, crown ethers and cryptates.

In most cases, the halogen exchange reaction is sluggish and tends to form product mixtures in which yields of polyfluorinated aromatics are relatively low, especially if the haloaromatic compound used is a polyhaloaromatic compound free from activating functionality such as nitro or carbonyl. For example, with hexachlorobenzene and potassium fluoride, typical product mixtures contain a mixture of co-products including hexafluorobenzene together with various chlorofluorobenzenes.

In now commonly-owned application Ser. No. 08/754, 338, filed Nov. 22, 1996, Igor Bildinov et al. describe a significant improvement in halogen exchange technology, namely that aminophosphonium compounds such as one or more tetra(dihydrocarbylamino)phosphonium halides are effective catalysts for halogen exchange reactions. Significant improvements in yields of desired products were achieved by conducting the reaction with a suitably-stirred mixture of reactants and catalyst in the form of finely divided solids.

Tetra(dihydrocarbylamino)phosphonium halides, which are relatively uncommon materials, can be prepared using the method described by Koidan, Marchenko, Kudryavtsev, and Pinchuk, *Zh. Obshch. Khim.*, 1982, 52, 2001, an English language translation of which is available from Plenum Publishing Corporation. A procedure which has been used for preparing tetra(diethylamino)phosphonium bromide involves the following four steps (where Et represents an ethyl group):

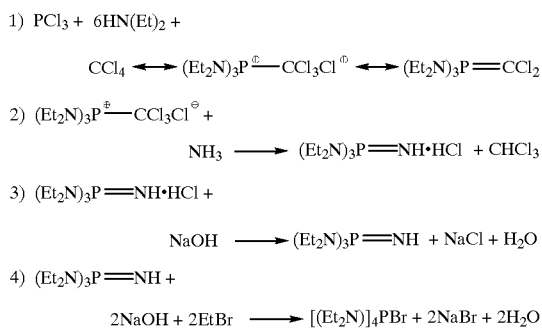

In this procedure, carbon tetrachloride and phosphorus trichloride are charged to the reactor followed by the slow addition of diethyl amine at low temperature (30° C. maximum). This results in the formation of dichloromethylene phosphoroamidite intermediate. Ammonia (gas) is then charged to the reactor resulting in the formation of an imino hydrochloride phosphoroamidite intermediate. Following a period of stirring, the reactor contents are filtered, and the filtrate is concentrated by evaporation under vacuum. The concentrated filtrate is then treated with sodium hydroxide solution causing the formation of the free base imino phosphoroamidite. This is extracted with dichloromethane. The extracted solution is dried with calcium chloride and the dichloromethane is removed by evaporation. The solid product is mixed with sodium hydroxide and bromoethane is charged. This results in the formation of the product tetra(diethylamino)phosphonium bromide. The product is then extracted with dichloromethane. The extract is dried and the dichloromethane is removed by evaporation. The crude product is then recrystallized from a mixture of dichloromethane and diethyl ether. The recrystallized, wet, product is then dried.

Despite the above advances in the art, it would be extremely desirable and economically advantageous if a way could be found to still further increase the efficiency of halogen exchange reactions performed using tetra (dihydrocarbylamino)phosphonium halide catalysts. It is this need to which the present invention is addressed.

SUMMARY OF THE INVENTION

This invention makes it possible to more effectively utilize the catalysts described in the co-pending Bildinov et al. application, and thus provides process technology enabling a wide variety of halogen exchange reactions to be conducted with high efficiency as a slurry process suitable for operation in large scale industrial facilities.

In accordance with one aspect of this invention, it has been found that a halogen exchange reaction between an alkali metal fluoride and a haloaromatic compound having at least one halogen atom of atomic number greater than 9 on an aromatic ring in the presence of a tetra (dihydrocarbylamino)phosphonium halide catalyst can be conducted more efficiently if the tetra(dihydrocarbylamino)

phosphonium halide is subjected preliminary processing to remove therefrom, or at least substantially reduce the content therein of, certain co-produced components comprising one or more amidophosphoxides and especially quaternary ammonium halides. This is accomplished by a pretreating process of this invention, which comprises:

a) contacting the impure tetra(dihydrocarbylamino) phosphonium halide with a liquid cyclic ether under conditions effective to dissolve the tetra(dihydrocarbylamino) phosphonium halide and leave at least a portion of said impurities comprising at least quaternary ammonium halide or amidophosphoxide remaining in the solid state;

b) separating the solids and the liquid phase of a) from each other;

c) mixing an anhydrous non-solvent for the tetra (dihydrocarbylamino)phosphonium halide with the liquid phase from b) to precipitate the tetra(dihydrocarbylamino) phosphonium halide; and d) separating the precipitated tetra(dihydrocarbylamino) phosphonium halide solids and the liquid phase of c) from each other.

It has been found that lower alkyl ethers such as ethyl ether ($Et_2O$) are highly suitable as non-solvents for use in c) above.

In another aspect of this invention a new catalytic halogen exchange reaction is provided using as catalyst a tetra (dihydrocarbylamino)phosphonium halide catalyst pretreated as above, together with an alkali metal fluoride as the fluorine source. The process enables production of a wide variety of fluorinated aromatic compounds under relatively mild reaction conditions. Moreover, the process is applicable to use as starting materials of haloaromatic compounds containing one or more halogen atoms other than fluorine, including compounds which are devoid of activating groups, as well as compounds which possess one or more activating groups in the molecule. In fact, the process is especially well adapted for polyfluorination of perhaloaromatic compounds such as hexachlorobenzene, hexabromobenzene, pentachlorofluorobenzene, tetrachlorodifluorobenzene, trichlorotrifluorobenzene, dichlorotetrafluorobenzene, etc., which have no activating group in the molecule. In addition, the catalyzed process can be conducted with smaller excesses of the alkali metal fluoride than generally required in prior processes.

Thus, in accordance with this invention there is also provided an improved halogen exchange process. More particularly, in a halogen exchange process which comprises heating a mixture formed from ingredients comprising (i) at least one finely-divided alkali metal fluoride, (ii) at least one haloaromatic compound having on an aromatic ring at least one halogen atom of atomic number greater than 9, and (iii) a catalyst, at one or more reaction temperatures at which at least one said halogen atom of said haloaromatic compound is replaced by a fluorine atom, the improvement comprises using as said catalyst ingredient at least one tetra (dihydrocarbylamino)phosphonium halide which has been pretreated by a process as described above.

In a preferred embodiment of this invention, the process is conducted using as the initial haloaromatic compound(s) for the halogen exchange, at least one haloaromatic compound that is devoid of any activating functional group on the aromatic ring to which the halogen atom of atomic number greater than 9 is bonded.

A particularly preferred embodiment involves using as the initial haloaromatic ingredient to be subjected to the halogen exchange processing, one or more haloaromatic compounds that are not only devoid of any activating functional group on the aromatic ring to which the halogen atom of atomic number greater than 9 is bonded, but in addition have no hydrogen atom on that aromatic ring. Especially preferred haloaromatic compounds of this type are perhaloaromatic compounds of the formula $C_6Cl_nBr_mF_p$ where n is from 0 to 6, m is from 0 to 6 and p is from 0 to 5, and where the sum of n, m and p is 6. Compounds in which m is zero have been used with outstanding success.

Another preferred embodiment includes conducting the process of this invention such that the mixture, at least when heated to one or more reaction temperatures, is predominately a mixture of solids dispersed or slurried in a continuous liquid phase. Operations wherein the continuous liquid phase comprises at least one halogen-free, polar, anhydrous or substantially anhydrous aprotic solvent constitute additional preferred embodiments of this invention.

These and other embodiments, features and advantages of this invention will be further apparent from the ensuing description, accompanying drawing, and appended claims.

FURTHER DESCRIPTION OF THE INVENTION

Tetra(Dihydrocarbylamino)Phosphonium Halides

Figure 1:
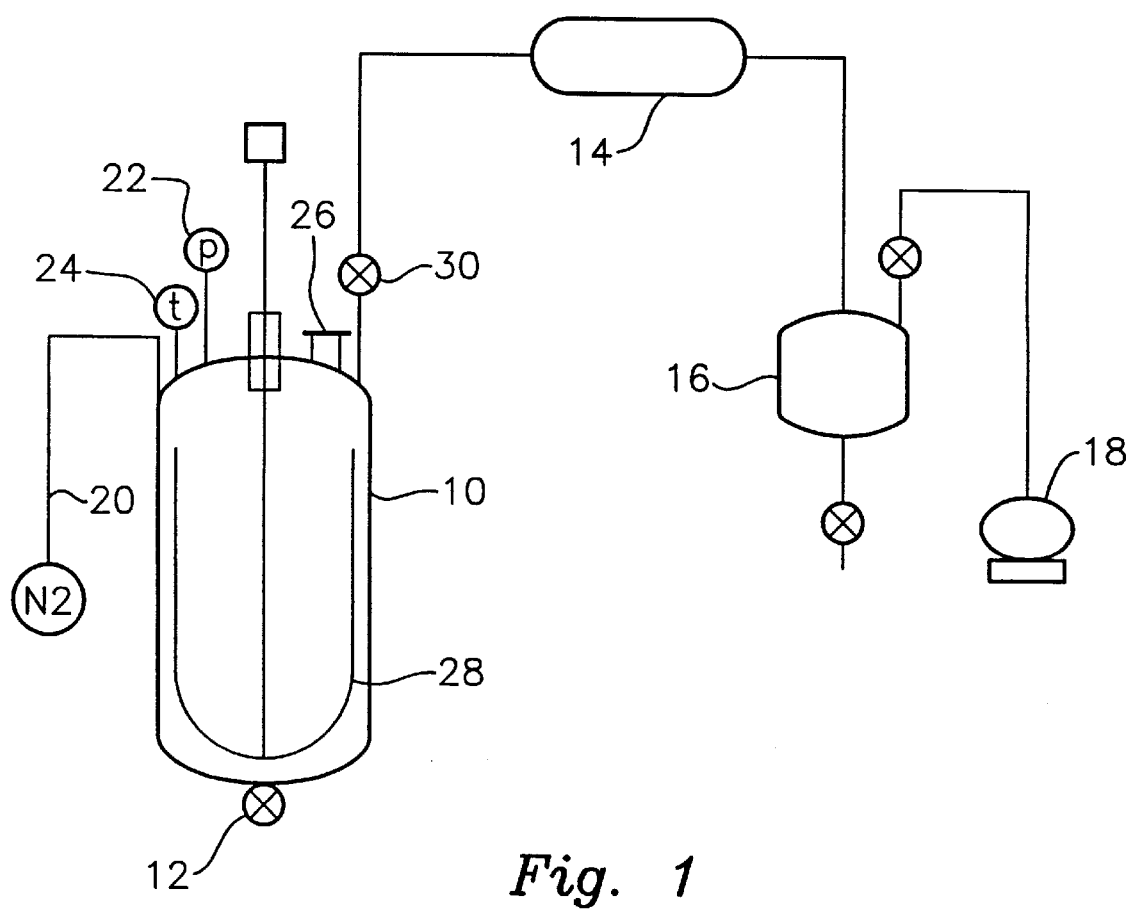
FIG. 1 illustrates schematically a batch type plant facility for conducting the process without use of an ancillary solvent/diluent.

Tetra(dihydrocarbylamino)phosphonium halides can be represented by the formula:

$$(R_2N)_4P^{\oplus} \: X^{\ominus}$$

where each R is, independently, a hydrocarbyl group, preferably an alkyl group, and X is a halogen atom, preferably a fluorine or bromine atoms, and most preferably a bromine atom. Examples of such aminophosphonium compounds are:

tetrakis(diethylamino)phosphonium fluoride
tetrakis(dibutylamino)phosphonium bromide
tris(diethylamino)(dipropylamino)phosphonium iodide
tetrakis(dibutylamino)phosphonium iodide
tris(dibutylamino) (diethylamino)phosphonium iodide
tris(dipropylamino)(diheptylamino)phosphonium iodide
tetrakis(dipropylamino)phosphonium bromide
tris(diethylamino)(dihexylamino)phosphonium iodide
tris(diethylamino)(dibutylamino)phosphonium iodide
tris(dipropylamino)(heptylpropylamino)phosphonium iodide
tetrakis(dipropylamino)phosphonium iodide
tris(dipropylamino)(ethylpropylamino)phosphonium iodide
tetrakis(diethylamino)phosphonium iodide
tetrakis(diethylamino)phosphonium bromide
tetrakis(diphenylamino)phosphonium bromide
tetrakis(di-m-tolylamino)phosphonium bromide
tetrakis(dibenzylamino)phosphonium bromide
tetrakis(dicyclohexylamino)phosphonium bromide
tetrakis(dioctylamino)phosphonium bromide
tetrakis(didecylamino)phosphonium bromide
tetrakis(diethylamino)phosphonium chloride.
tetrakis(dipropylamino)phosphonium chloride
tetrakis(dibutylamino)phosphonium chloride
tetrakis(dihexylamino)phosphonium chloride.

A method for the preparation of such compounds is described in Koidan, Marchenko, Kudryavtsev, and Pinchuk, Zh. Obshch. Khim., 1982, 52, 2001, an English language translation of which is available from Plenum Publishing Corporation.

As noted above, a typical process for producing tetrakis (dihydrocarbylamino)phosphonium halides involves (1)

charging carbon tetrachloride and phosphorus trichloride to the reactor followed by the slow addition of dihydrocarbyl amine at low temperature (30° C. maximum). This results in the formation of a dichloromethylene phosphoroamidite intermediate. (2) Ammonia (gas) is then charged to the reactor resulting in the formation of an imino hydrochloride phosphoroamidite intermediate. Following a period of stirring, the reactor contents are filtered, and the filtrate is concentrated by evaporation under vacuum. (3) The concentrated filtrate is then treated with sodium hydroxide solution causing the formation of the free base imino phosphoroamidite. This is extracted with dichloromethane. The extracted solution is dried with calcium chloride and the dichloromethane is removed by evaporation. (4) The solid product is mixed with sodium hydroxide and a hydrocarbyl halide (e.g., alkyl chloride or bromide, cycloalkyl chloride or bromide, aryl chloride or bromide) is charged. This results in the formation of the product tetra(dihydrocarbylamino) phosphonium chloride or bromide. The product is then extracted with dichloromethane. The extract is dried and the dichloromethane is removed by evaporation. The crude product is then recrystallized, e.g., from a mixture of dichloromethane and diethyl ether. The recrystallized, wet, product is then dried. The above procedure can be represented by the following generalized equations wherein R is a hydrocarbyl group and X is a halogen atom:

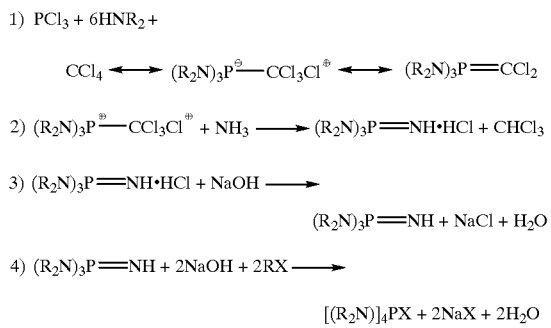

Pretreatment of Tetra(Dihydrocarbylamino)Phosphonium Halides

In a preferred pretreatment process of this invention, the tetrakis(dihydrocarbylamino)phosphonium halide is dissolved at ambient temperature (e.g., in the range of about 0 to about 60° C., and preferably in the range of about 20 to about 30° C.) in a cyclic ether in which common impurities comprising quaternary ammonium halide in the tetrakis (dihydrocarbylamino)phosphonium halide are substantially insoluble (e.g., a cyclic ether in which at least a portion, e.g., at least about 10% by weight and preferably at least about 25% by weight, of such impurities remain in the solid state at the selected temperature). In conducting this step of the process it is desirable to use a sufficient amount of cyclic ether to dissolve the quantity of the tetrakis (dihydrocarbylamino)phosphonium halide being treated without at the same time using a substantial excess of the cyclic ether. In this way materials handling is simplified and the operation is rendered more efficient than if an excessive amount of cyclic ether were used. Generally speaking, therefore, the smaller the excess of cyclic ether used above that required to dissolve the tetrakis(dihydrocarbylamino) phosphonium halide under the conditions being used, the better.

Cyclic ethers which can be used in this operation include tetrahydrofuran, 2-methyltetrahydrofuran, 3-methyltetrahydrofuran, 2,5-dimethyltetrahydrofuran, methyl tetrahydrofurfuryl ether, tetrahydropyran, 3-methyltetrahydropyran, 1,3-dioxolane, 1,3-dioxane, 2-methyl-1,3-dioxolane, 4-methyl-1,3-dioxolane, 1,4-dioxane, 4-methyl-1,3-dioxane, 3,4-dihydro-2H-pyran, and similar liquid cyclic ethers.

The next step in the pretreatment process involves separating the solids and the liquid cyclic ether organic phase from each other, as by a physical separation procedure such as filtration, centrifugation, decantation, or like procedure. Then, an anhydrous non-solvent for the tetra (dihydrocarbylamino)phosphonium halide is mixed with the liquid cyclic ether organic phase to precipitate the tetra (dihydrocarbylamino)phosphonium halide. This operation can be conducted at temperatures in the range of about −10 to about 40° C., and is typically conducted at ambient room temperature. As candidate precipitating solvents, aliphatic monoethers such as diethylether, ethylmethylether, ethylpropylether, methylpropylether, dipropylether, dibutylether, and like liquid ethers having no more than about 8 carbon atoms are deemed suitable. Preferred is diethylether itself ($Et_2O$). A few simple tests will identify other suitable precipitating solvents. Thereafter the precipitated tetra(dihydrocarbylamino)phosphonium halide solids and the resulting liquid phase are separated from each other, again by a suitable physical separation procedure, such as any of those mentioned above.

The proportions of the solvent and non-solvents are dependent upon such factors as the particular tetra (dihydrocarbylamino)phosphonium halide be pretreated, the temperature being used, and the solvent and non-solvent being used. Thus in any given situation it is desirable to perform a few preliminary tests with the selected materials and under the selected conditions in order to optimize the proportions for use in subsequent pretreatments with such materials under the selected conditions.

Typically, the impure tetra(dihydrocarbylamino) phosphonium halide to be pretreated pursuant to this invention will contain at least 10% by weight of impurities comprising at least one quaternary ammonium halide and/or at least one amidophosphoxide.

Catalyst Ingredient(s)

The catalyst ingredient used in the halogen exchange embodiments this invention is at least one tetra (dihydrocarbylamino)phosphonium halide ingredient that has been pretreated pursuant to this invention. One or more other co-catalysts may also be included, if desired, as long as at least one pretreated tetra(dihydrocarbylamino) phosphonium halide catalyst ingredient is charged, concurrently or in any sequence, into the reaction zone or reaction mixture. Use of the tetra(dihydrocarbylamino)phosphonium halide catalyst without use of a co-catalyst is currently deemed preferable.

One preferred group of pretreated tetra (dihydrocarbylamino)phosphonium halide catalysts in the form as charged to the reactor is comprised of the tetra (dialkylamino)phosphonium chlorides and/or bromides. Of these, the catalyst ingredient is more preferably one or more tetra(dialkylamino)phosphonium bromides in which the alkyl groups can be the same or different and each has up to about 12 carbon atoms. At present, the most preferred compound is tetrakis(diethylamino)phosphonium bromide which has been pretreated pursuant to this invention.

In conducting the halogen exchange reaction, the pretreated tetra(dihydrocarbylamino)phosphonium halide catalyst is used in catalytically effective amounts, and such amounts typically fall in the range of about 3 to about 6 mol %, and preferably in the range of about 4 to about 5 mol %, based on the total amount (in mols) of the haloaromatic compound(s) with which the catalyst is being associated in the reaction zone.

Haloaromatic Ingredient

Any aromatic compound that has at least one replaceable halogen atom other than fluorine on the aromatic ring is a candidate ingredient for use in the process. The compound may have a homocyclic aromatic nucleus (i.e., at least one benzene ring system) or a heteroaromatic ring system. Also, the compound may contain one or more activating groups such as nitro, nitroso, carbonyl, cyano, sulfonic acid, etc., or it may be devoid of any such group. The compound contains one or more chlorine, bromine or iodine atoms, or any combination of Cl, Br, and/or I atoms on the aromatic ring and may also have one or more such halogen atoms on one or more side chains and/or on one or more non-aromatic homocyclic or heterocyclic rings bonded or fused to the aromatic ring system. In addition the compound may contain one or more fluorine atoms anywhere in the molecule including one or more ar-fluorine atoms provided the compound has at least one aromatic ring that contains at least one replaceable ar-halogen atom other than fluorine. The hetero atom in the halo-substituted aromatic ring where the fluorine substitution is desired is from 1 to 3 nitrogen atoms (e.g., the compound is, or has at least the ring system of, an ar-halopyridine, an ar-halopyridazine, an ar-halopyrimidine, an ar-halopyrazine, an ar-halotriazine where at least one ar-halogen atom is other than a fluorine atom). Other hetero atoms which can be present in side chains or additional ring systems of the compound include one or more nitrogen, oxygen, sulfur, phosphorus, boron or silicon atoms, or combinations of two or more of these. Generally speaking, the haloaromatic ingredient may contain in the range of up to 50 carbon atoms in the molecule, and preferably contains in the range of up to 20 carbon atoms in the molecule.

Preferred are haloaromatic compounds that are devoid of any activating group(s) in the molecule, as these usually undergo a halogen exchange reaction much less readily than their counterparts which have activating functionality in the molecule.

As between the homocyclic and heterocyclic haloaromatics, the homocyclic haloaromatics are preferred ingredients. As noted above, haloaromatics that are devoid of any activating functional group on the aromatic ring to which the halogen atom of atomic number greater than 9 is bonded and in addition, are devoid of any hydrogen atom on that aromatic ring constitute another preferred category of haloaromatic ingredient or feed material for the process. Especially preferred haloaromatic compounds of this type are perhaloaromatic compounds of the formula $C_6Cl_nBr_mF_p$ where n is from 0 to 6, m is from 0 to 6 and p is from 0 to 5, and where the sum of n, m and p is 6. Compounds in which m is zero are especially desirable ingredients because of good reactivity in the process and generally lower cost. Moreover, there is a particularly pressing present need for methods for effectively producing polyfluorobenzenes, especially chloropentafluorobenzene and hexafluorobenzene, from their polychloro analogs such as hexachlorobenzene, pentachlorofluorobenzene, tetrachlorodifluorobenzene, trichlorotrifluorobenzene, or dichlorotetrafluorobenzene, or mixtures of any two or more of these, a need fulfilled by this invention.

Also fulfilled by this invention is the need for a method for effectively producing bromopentafluorobenzene from its polybromo analogs such as hexabromobenzene, pentabromofluorobenzene, tetrabromodifluorobenzene, tribromotrifluorobenzene, or dibromotetrafluorobenzene, or mixtures of any two or more of these.

Other haloaromatic compounds which can be converted into ar-fluorinated compounds by use of this invention include, for example, mono-, di-, tri-, tetra- and pentachlorobenzenes, and bromo and iodo analogs thereof; mono and polychloro, bromo and iodo naphthalenes, tetrahydronaphthalenes, acenaphthalenes, biphenyls and terphenyls; alkyl- and haloalkyl-substituted analogs of the foregoing; chloro, bromo and iodo diarylethers and monoalkylmonoaryl ethers; 2-chloronitrobenzene; 4-chloronitrobenzene; 2,4-dinitrochlorobenzene; 3,4-dichloronitrobenzene; 3-chloro-4-fluoronitrobenzene; 2,4,6-trichloropyrimidine; tetrachloropyrimidine; 2-chlorobenzonitrile; 4-chlorobenzonitrile; pentachlorobenzonitrile; tetrachloroisophthalonitrile; 2-chloropyridine; 2,5-dichloropyridine; pentachloropyridine; 4-chlorophthalic anhydride; and still other similar compounds, such as are referred to in U.S. Pat. No. 4,684,734 to Kaieda, et al.

Alkali Metal Fluoride Ingredient

Potassium fluoride, rubidium fluoride, and cesium fluoride are the preferred alkali metal halides used in the practice of this invention because of their higher reactivity in the exchange reaction. However, sodium fluoride can be used, especially where the haloaromatic ingredient has activating functionality on the haloaromatic ring, and in cases where only partial replacement of ar-chloride, ar-bromide or ar-iodide is desired.

Combinations of any two or more of the alkali metal fluorides can be used, including combinations in which lithium fluoride is present. Thus, mixtures of potassium fluoride, rubidium fluoride and/or cesium fluoride together with sodium fluoride or lithium fluoride, or both, can also be used if desired, although this is not recommended. To enhance its reactivity, the alkali metal fluoride should be in finely-divided or powdery anhydrous form. Potassium fluoride is the preferred fluorinating agent as it is the most cost effective reagent. One convenient way of ensuring that the fluorinating agent is suitably anhydrous is to form a slurry of the fluoride salt in a suitable volatile hydrocarbon such as benzene that forms an azeotrope with water, and heat the mixture to dryness, while of course suitably handling and disposing of the vapors. A particularly useful form of potassium fluoride for use in the process is the active form of KF produced using the procedure described by T. P. Smyth, A. Carey and B. K. Hodnett in *Tetrahedron*, Volume 51, No. 22, pp. 6363–6376 (1995). In brief, the procedure involves recrystallizing KF from a methanol solution by slow evaporation of the solvent, followed by drying at 100° C. Another useful form of potassium fluoride is KF dispersed on $CaF_2$. This material is described by J. H. Clark, A. J. Hyde and D. K. Smith in *J. Chem. Soc. Chem. Commun,* 1986, 791. Other activated forms of KF such as spray dried KF (N. Ishikawa, et al. *Chem. Letts,* 1981, 761), and freeze dried KF (Y. Kimura, et al. *Tetrahedron Letters,* 1989, 1271) can be used. It is also deemed possible to apply one or more of the foregoing activating procedures to other alkali metal fluorides such as cesium fluoride and/or sodium fluoride. The entire disclosure of each of the four papers cited in this paragraph is incorporated herein by reference.

To enhance its reactivity, the alkali metal fluoride as charged to the reaction mixture is preferably in finely-divided or powdery anhydrous or substantially anhydrous form, i.e., it should not contain, if any, more than about 3000 parts per million (ppm) of water on a weight basis. Potassium fluoride is the preferred fluorinating agent as it is the most cost-effective reagent, and most preferably it will have a water content, if any, below about 1000 ppm. Ordinarily the alkali metal fluoride particles should have an average surface area of at least about 0.20 m²/g. In this connection, the larger the average surface area of the alkali metal fluoride particles, the better. Thus it is preferred that the alkali metal fluoride initially have an average surface area of at least about 0.40 m²/g, and more preferably at least about 0.80 m²/g. For example, as charged to the reactor in the practice of this invention, spray dried potassium fluoride with a typical water content of about 1000 ppm and an average surface area of about 0.85 m²/g has been found to give a reaction rate that is approximately four times the rate given under the same conditions by spray dried potassium fluoride with an average surface area of about 0.25 m²/g.

The proportions of alkali metal fluoride to the haloaromatic ingredient(s) being used can be varied. In theory there is no upper limit on the amount of alkali metal fluoride used relative to the amount of haloaromatic compound(s) used. If a very large excess of alkali metal fluoride is used relative to the amount of replaceable halogen present in the haloaromatic ingredient(s) present, the latter becomes the limiting reactant and the excess alkali metal halide remains as such. When the reaction is performed in the absence of an ancillary diluent, an excess amount of the alkali metal fluoride can serve to facilitate stirring or other agitation of the reaction mixture, and thus to this extent use of a suitable excess of alkali metal fluoride can be beneficial. Nevertheless, beyond a certain level of excess alkali metal fluoride, common sense and practicality come into play. Thus ordinarily the amount of alkali metal fluoride will not exceed about 10 or 15 mols per mol of replaceable halogen in the initial haloaromatic ingredient(s) used, and in most cases will be less than this. If on the other hand the amount of replaceable halogen in the haloaromatic ingredient(s) used exceeds the molar quantity of alkali metal fluoride used, the latter becomes the limiting reactant. Thus in most cases this factor will also be taken into consideration when selecting the proportions for use in any given reaction. Generally speaking, the reactants will often be employed in proportions falling in the range of from about 0.8 to about 5 mols of alkali metal fluoride per mol of replaceable halogen in the haloaromatic ingredient(s) used therewith, and in some preferred cases such as where an ancillary diluent is employed, the reactants will be charged in proportions in the range of from about 1 to about 3 mols of alkali metal fluoride per mol of replaceable halogen in the haloaromatic ingredient(s) used therewith.

Co-catalyst Ingredient(s)

The tetra(dihydrocarbylamino)phosphonium halide catalysts are effective when utilized as the only catalyst component charged directly or indirectly (i.e., after admixture with one or more other components being charged to the reaction system). Such catalytic mode of operation is preferred. However, as noted above, one or more co-catalyst ingredients may be used, if desired.

One type of such co-catalyst materials is comprised of one or more crown ethers or crypt compounds. These compounds, sometimes referred to as "cage compounds" can prove helpful in further enhancing the reactivity of the alkali metal fluoride. See in this connection, U.S. Pat. No. 4,174,349 to Evans, et al. A full description of the crown ethers and the crypt compounds is provided in the Evans, et al. patent and references cited therein relating to these materials, namely U.S. Pat. No. 3,687,978; J. J. Christensen, et al., *Chem. Rev.,* 1974, 74, 351; J. S. Bradshaw, et al., *Heterocycl. Chem.,* 1974, 11, 649; C. J. Pedersen, et al., *Angew. Chem. Int. Ed. EngL.,* 1972, 11, 16; the Technical Bulletin of PCR Incorporated entitled KRYPTOFIX; and *J. Org. Chem,* 1977, Vol 42, No. 10, 2A. The crown ether or crypt compound is used in a catalytically effective amount, which typically is in the range of 0.01 to 1 mol per mol of haloaromatic compound(s) in the reaction mixture.

Another type of co-catalyst that can be used is composed of (i) at least one polyvalent inorganic fluoride of boron, aluminum, tin, phosphorus, titanium, zirconium, hafnium, or silicon, or (ii) at least one double salt of the polyvalent inorganic fluoride and alkali metal fluoride, or (iii) a combination of (i) and (ii), with the proviso that the inorganic fluoride of (i), (ii) and (iii) is in a stable valency state so that (i), (ii) and (iii), as the case may be, has no oxidizing properties. U.S. Pat. No. 3,453,337 to Bennett, et al., reports that in the uncatalyzed reaction between hexachlorobenzene and KF or NaF, the inclusion of compounds of the types (i), (ii) and (iii) above provides enhanced product yields using milder reaction conditions and shorter reaction times. Examples of suitable polyvalent compounds include $LiBF_4$, $NaBF_4$, $KBF_4$, $K_2SnF_6$, $KPF_6$, $K_2SiF_6$, $Na_2TiF_6$, $K_2TiF_6$, $Na_2ZrF_6$, $K_2ZrF_6$, $Na_2HfF_6$, $K_2HfF_6$, among others. Such compounds can be used in catalytically effective amounts of up to 50% or more of the weight of the alkali metal fluoride charged to the reaction mixture. Typically the amount will fall in the range of about 2 to about 25 % of the weight of alkali metal fluoride used.

Other co-catalysts which may be considered for use include quaternary ammonium salts such as described for example by J. Dockx, *Synthesis,* 1973, 441; C. M. Starks and C. Liotta, *Phase Transfer Catalysts,* 1978, Academic Press, New York; and W. P. Weber and G. W. Gokel, *Phase Transfer Catalysis in Organic Synthesis,* 1977, Springer-Verlag, Berlin-Heidelberg-New York); and metal carbonyls such as described by M. F. Semmelhack and H. T. Hall, *J. Am. Chem. Soc.,* 1974, 96, 7091.

The aminophosphonium catalyst and the above co-catalyst(s), if used, can vary both in function and in composition. As to function, they can serve to promote or enhance the fluorination exchange reaction, e.g., (a) by increasing reaction rate without affecting yield or selectivity, (b) by increasing yield or selectivity, or both, without affecting reaction rate, or (c) by increasing reaction rate and improving yield or selectivity, or both. Thus the term "catalyst" or "co-catalyst" is used herein to denote that the material in the manner used improves or enhances the reaction process in some way or other so that the inclusion or presence of that material or its progeny in the reaction mixture provides at least one beneficial consequence of its use. The mechanism by which it exerts its effect(s) is of no consequence, provided of course that the advantage(s) of its use outweigh(s) the disadvantage(s), if any, of its use.

As regards catalyst and co-catalyst composition, the material is identified herein as to its composition prior to being combined with any other substance being used in the process. After addition to, and/or mixing with, one or more other ingredients used in the process and/or during the course of the process itself, the catalyst may change in its composition, and if so, the resultant changed material, whatever its makeup and however many changes it may undergo, may be responsible in whole or in part for the functioning of the catalyst.

Halogen Exchange Process Conditions

The process can be conducted by dry mixing the finely-divided essentially anhydrous alkali metal fluoride, the haloaromatic compound having at least one halogen atom of atomic number greater than 9 on an aromatic ring, and a tetra(dihydrocarbylamino)phosphonium halide catalyst pretreated pursuant to this invention, and heating the mixture at one or more reaction temperatures at which at least one such halogen atom of the haloaromatic compound is replaced by a fluorine atom. Alternatively, the foregoing ingredients may be heated to one or more such reaction temperatures while in admixture with an ancillary solvent/diluent. The solvent or diluent used is preferably a polar aprotic solvent such as, for example, sulfolane (tetramethylene sulfone), N,N-dimethylformamide, N,N-dimethylacetamide, dimethylsulfone, dimethylsulfoxide, triglyme (triethylene glycol dimethyl ether), N-methyl pyrrolidinone, or benzonitrile, or mixtures of two or more of such materials, and like polar aprotic solvents that are in the liquid state at the reaction temperature selected for use, and more preferably that are also in the liquid state at 10° C. or below. Benzonitrile and ring-substituted liquid alkylbenzonitriles (e.g., o-methylbenzonitrile, m-methylbenzonitrile, etc.), and especially benzonitrile itself, are the preferred solvents. Another preferred aprotic solvent is nitrobenzene because of its excellent solvency characteristics and relatively low cost. Other solvent/diluents for use in the process are haloaromatics that are in the liquid state at least at, and preferably below, the reaction temperature(s) being employed. Examples include hexafluorobenzene, octafluorotoluene, perfluorodecalin, dichlorotetrafluorobenzene, trichlorotrifluorobenzene and tetrachlorodifluorobenzene. The last three such compounds are especially desirable as solvent/diluents when producing pentachlorofluorobenzene as they not only serve as solvent/diluents, but as reactants as well.

Whether the reaction mixture is formed with or without a solvent/diluent, the reaction mixture should be thoroughly agitated during the course of the reaction to ensure intimate contact among the different materials in the mixture. Thus use of mechanical agitation equipment such as mechanical stirrers, rocking autoclaves, or similar apparatus is highly recommended.

Reaction temperatures will typically be in the range of about 150° C. to about 350° C. and preferably in the range of about 170° C. to about 250° C. When the process is conducted as a slurry process using a liquid aprotic solvent or diluent, it is preferred to conduct the process at one or more temperatures in the range of about 200° C. to about 240° C. The reaction may be conducted at atmospheric, sub-atmospheric or super-atmospheric pressures. In many cases it is desirable as well as convenient to carry out the reaction in a closed system at autogenous pressures. Reaction periods will typically fall in the range of about 2 to about 48 hours, and preferably in the range of about 5 to about 20 hours. It will be appreciated that on the basis of this disclosure, departures from any of the ranges of proportions and/or reaction conditions given above may be made whenever such departures are deemed necessary or desirable.

Reaction temperatures will typically be in the range of about 150° C. to about 350° C. and preferably in the range of about 170° C. to about 250° C., and more preferably in the range of about 170° C. to about 220° C. The reaction may be conducted at atmospheric, sub-atmospheric or super-atmospheric pressures. In many cases it is desirable as well as convenient to carry out the reaction in a closed system at autogenous pressures. Alternatively, the reaction may be carried out in a liquid phase under reflux conditions. Reaction periods will typically fall in the range of about 2 to about 48 hours, and preferably in the range of about 5 to about 20 hours. It will be appreciated that on the basis of this disclosure, departures from any of the ranges of proportions and/or reaction conditions given above may be made whenever such departures are deemed necessary or desirable.

The following examples are for the purpose of illustration and not limitation. Example 1 illustrates the present pretreatment process to remove, or at least reduce the amount of, impurities such as quaternary ammonium halide. In Examples 2 and 3 the pretreated, purified catalyst was used, and in the Comparative Example the original non-pretreated catalyst was used. In Example 2 the halogen exchange reaction was performed on a semi-continuous basis whereas in Example 3, a batch-type operation was used. A comparison between Example 3 and the Comparative Example, which were performed in the same way, illustrates the advantages of using a pretreated, purified catalyst when practicing the halogen exchange reaction.

EXAMPLE 1
Catalyst Pretreatment

To a 1-liter flask containing 156 grams of tetrahydrofuran at ambient room temperature was added with stirring 38.90 grams of tetrakis(diethylamino)phosphonium bromide catalyst (Chordip Limited, England, ca. 75% purity). By use of GC/MS and NMR it was determined that approximately 95% of the impurities in this product were as follows:

| Impurity | Approximate wt % in the Product |
| --- | --- |
| Dichlorobromomethane | 0.33% |
| Diethylformamide | 0.06% |
| Tetraethyl urea | 0.30% |
| Ethoxy-N,N,N',N'-tetraethylamidophosphoxide | 1.98% |
| Tris(diethylamido)phosphoxide | 12.2% |
| Bis(diethylamido)ethylaminophosphoxide | 0.13% |
| Tetraethylammonium bromide | 7.0% |

The residual insoluble material (2.8 grams) was filtered from the solution, and was determined by $^1$H-NMR to be primarily tetraethylammonium bromide. To the tetrahydrofuran solution of the catalyst was then added 245 grams of anhydrous diethyl ether resulting in the precipitation of the tetrakis(diethylamino)phosphonium bromide catalyst. The solid catalyst was then filtered and dried under full vacuum at about 50° C. for one hour. The purified catalyst (29.8 grams) was analyzed by $^{31}$P-NMR and was found to be at least 95% pure.

EXAMPLE 2
Semi-Continuous Halogen Exchange Reaction

To a 1-liter stainless steel stirred pressure reactor was added a solution of 12 grams of purified catalyst from Example 1 in 421 grams of benzonitrile (Aldrich, <50 ppm water), 164 grams of spray-dried potassium fluoride (Hashimoto Chemical Corporation, Japan, 0.87 m$^2$/g), and 115 grams of hexachlorobenzene. The overhead of the reactor comprised of a ½ inch-OD column packed with 15-inch long Pro-Pak® packing, an air-cooled partial condenser (also known as a knockback condenser), an air-cooled total condenser, and a product receiver with a back-pressure control valve. The reaction mixture, a slurry, was heated and maintained at 218–220° C. for 5 hours while maintaining the system pressure at 14 psig and the column distillate temperature at 140° C. The vaporized perhalobenzenes, predominately chloropentafluorobenzene and some hexafluorobenzene, were carried to the overhead about as soon as they were formed, and thereupon were condensed and recovered. Concurrently, other condensed perhalobenzenes were being returned from the knockback condenser to the reaction mixture. At the end of the 5-hour reaction period, the heating was discontinued and all the volatile products remaining in the reactor were removed by distillation by application of progressively increased vacuum to the system in order to recover all volatile products formed in the reaction. The entire distillate product mixture was analyzed by gas chromatography. The yields, based on hexachlorobenzene, and were 2.5% hexafluorobenzene, 58.6% chloropentafluorobenzene, 23.8% dichlorotetrafluorobenzene, and 7.5% trichlorotrifluorobenzene.

EXAMPLE 3
Batch-Type Halogen Exchange Reaction

A solution of 12.0 grams of purified tetrakis (diethylamino)phosphonium chloride catalyst from Example 1 in 420 grams of benzonitrile (Aldrich, <50 ppm water) was charged to a 1-liter stainless steel stirred pressure reactor. Spray-dried potassium fluoride (164 grams, Hashimoto Chemical Corporation, Japan, 0.87 $m^2/g$) and hexachlorobenzene (115 grams) were then added to the reactor. The reaction mixture was reacted for 5.5 hours at 220° C. The heating was then discontinued and all the volatile products were removed by simple distillation at progressively increased vacuum. The distillate mixture was analyzed by gas chromatography. The yields, based on hexachlorobenzene, were 24.4% hexafluorobenzene, 39.9% chloropentafluorobenzene, 21.9% dichlorotetrafluorobenzene, and 8.1% trichlorotrifluorobenzene.

Comparative Example

A solution of 15.1 grams of tetrakis(diethylamino) phosphonium bromide catalyst (Chordip Limited, England, 75% purity) and 420 grams of benzonitrile (Aldrich, <50 ppm water) was charged to a 1-liter stainless steel stirred pressure reactor. Spray-dried potassium fluoride (164 grams, Hashimoto Chemical Corporation, Japan, 0.87 $m^2/g$) and hexachlorobenzene (115 grams) were then added to the reactor. The reaction mixture was reacted for 6.5 hours at 220° C. The heating was then discontinued and all the volatile products were removed by simple distillation at progressively increased vacuum. The distillate mixture was analyzed by gas chromatography. The yields, based on hexachlorobenzene, were 34.7% hexafluorobenzene, 37.7% chloropentafluorobenzene, 12.3% dichlorotetrafluorobenzene, and 3.9% trichlorotrifluorobenzene.

When conducting the halogen exchange reaction as a solid state reaction (i.e., no ancillary solvent or diluent is used) it is preferred to use a facility of the type described by Igor Bildinov et al. in now commonly-owned application Ser. No. 08/754,338, filed Nov. 22, 1996, and as schematically depicted in FIG. 1 hereof. The facility comprises a 50-liter capacity stainless steel reactor (316S) 10 fitted with an electrical heating system (not depicted), bottom discharge valve 12, vapor condenser 14, receiver 16, vacuum system 18, a pressure release system (not depicted) that operates via the overheads, nitrogen line 20 for vacuum breaking, pressure gauge/monitor 22, temperature gauge/monitor 24, and manway 26 for solids charging. Reactor 10 is capable of operating at working pressures up to 125 psi, and vacuum system 18 has the capability of operating to 10 mmHg pressure. Agitator 28 is preferably a modified gate-type agitator having scraping knife-edges on the gate agitator to minimize sticking of the semi-molten paste-like reaction mass especially at the reactor wall. The facility should also include a spray drier (not depicted).

In the operation of the facility freshly prepared anhydrous potassium fluoride is used for each batch. This is conveniently prepared by forming a 40% weight/volume solution of potassium fluoride, heating the solution to the boiling point and pumping the solution via a dried atomizer into a drier operated at 350–400° C., e.g., 370° C. The dry powder is placed into suitable containers and used immediately. Alternatively, an activated form of KF such as referred to above, or a commercially available spray dried KF (whether milled or not milled), can be used. Before initiating a reaction, steps should be taken to ensure that the reactor 10 and the overheads are clean and dry, that all systems are operational, and that all raw materials (including tetra (dihydrocarbylamino)phosphonium halide catalyst pretreated pursuant to this invention) are available for use. In addition the system should be checked to ensure that the bottom valve 12 is closed. If there is any doubt as regards vessel dryness, the reactor should be heated to 105° C. with full vacuum applied for two hours. After two hours the vessel should be allowed to cool while under vacuum. At ambient temperature the vacuum is then broken with nitrogen, and at this point the reaction procedure may be commenced.

At the start of the batch operation, reactor agitator 28 should be activated to be sure that the agitator is running smoothly. To the reactor with the agitator in operation, 21 kg of dry potassium fluoride powder is charged via manway 26. Then through the manway are charged 15 kg of hexachlorobenzene followed by 0.96 kg of the pretreated tetra (dihydrocarbylamino)phosphonium halide catalyst such as tetrakis(diethylamino)phosphonium bromide. Manway 26 and valve 30 are closed. The reactor contents are then heated over a period of one hour to 180° C. It is important to use this rapid heating to ensure sufficient agitation of this particular reaction mixture. During the heating the pressure in the reactor rises gradually. When the reactor contents reach 180° C., the reactor heating controls are adjusted to provide a heating rate increase of 4° C. per six hours. The reactor contents are allowed to heat up over this rate over 42 hours (7 increments of temperature increase for a total temperature increase of 28° C.). Slow heating at this stage of the process is important to ensure adequate mixing of this particular reaction mixture. At this point the reaction mixture should have reached a temperature of approximately 208° C. and the internal pressure of the reactor is monitored hourly. When the pressure does not vary between two successive hourly readings, the reaction can be deemed to have proceeded to completion. When the pressure becomes constant in the range of 75–100 psi the heating system is turned off and the reactor is allowed to cool. At this point valve 30 is cautiously opened to allow the pressure to vent from the reactor to condenser 14 and thence to receiver 16. When ambient pressure is reached in the reactor nitrogen is slowly introduced via nitrogen line 20. Vacuum system 18 is put into operation to provide a vacuum of about 725 mmHg to reactor 10. The nitrogen bleed to the reactor is slowly reduced while observing the rate of distillate recovery to receiver 16 to ensure that distillate recovery is not excessive. The vacuum is then gradually increased while continuing to monitor distillate recovery rate until maximum (flat) vacuum is achieved. When the system reaches ambient temperature the vacuum is broken with nitrogen, the vacuum system is shut off, and then the nitrogen bleed is discontinued. The reaction product mixture is then recovered from the reactor through valve 12. The reactor is cleaned with boiling aqueous caustic solution, washed with water and dried.

It is to be understood that the ingredients referred to by chemical name or formula anywhere in the specification or claims hereof, whether referred to in the singular or plural, are identified as they exist prior to coming into contact with another substance referred to by chemical name or chemical type (e.g., another reactant, a solvent, a diluent, or etc.). It matters not what preliminary chemical changes, transformations and/or reactions, if any, take place in the resulting mixture or solution or reaction medium as such changes, transformations and/or reactions are the natural result of bringing the specified reactants and/or components together under the conditions called for pursuant to this disclosure. Thus the reactants and other materials are identified as ingredients to be brought together in connection with performing a desired chemical reaction or in forming a mixture to be used in conducting a desired reaction. Accordingly, even though the claims hereinafter may refer to substances, components and/or ingredients in the present tense ("comprises", "is", etc.), the reference is to the substance or ingredient as it existed at the time just before it was first contacted, blended or mixed with one or more other substances or ingredients in accordance with the present disclosure. The fact that the substance or ingredient may have lost its original identity through a chemical reaction or transformation or complex formation or assumption of some other chemical form during the course of such contacting, blending or mixing operations, is thus wholly immaterial for an accurate understanding and appreciation of this disclosure and the claims thereof. Nor does reference to an ingredient by chemical name or formula exclude the possibility that during the desired reaction itself an ingredient becomes transformed to one or more transitory intermediates that actually enter into or otherwise participate in the reaction. In short, no representation is made or is to be inferred that the named ingredients must participate in the reaction while in their original chemical composition, structure or form.

Each and every patent or other publication referred to in any portion of this specification is incorporated in toto into this disclosure by reference, as if fully set forth herein.

This invention is susceptible to considerable variation in its practice. Therefore the foregoing description is not intended to limit, and should not be construed as limiting, the invention to the particular exemplifications presented hereinabove. Rather, what is intended to be covered is as set forth in the ensuing claims and the equivalents thereof permitted as a matter of law.

What is claimed is:

1. A process which comprises:
   a) contacting an impure tetra(dihydrocarbylamino) phosphonium halide with a liquid cyclic ether under conditions effective to dissolve the tetra (dihydrocarbylamino)phosphonium halide and leave at least a portion of said impurities comprising at least quaternary ammonium halide or an amidophosphoxide remaining in the solid state;
   b) separating the solids and the liquid phase of a) from each other;
   c) mixing an anhydrous non-solvent for the tetra (dihydrocarbylamino)phosphonium halide with the liquid phase from b) to precipitate the tetra (dihydrocarbylamino)phosphonium halide; and
   d) separating the precipitated tetra(dihydrocarbylamino) phosphonium halide solids and the liquid phase of c) from each other.

2. A process according to claim 1 wherein the tetra (dihydrocarbylamino)phosphonium halide ingredient used in a) comprises at least one tetra(dialkylamino)phosphonium halide.

3. A process according to claim 1 wherein the tetra (dihydrocarbylamino)phosphonium halide ingredient used in a) is at least one tetra(dialkylamino)phosphonium chloride and/or bromide.

4. A process according to claim 1 wherein the tetra (dihydrocarbylamino)phosphonium halide ingredient used in a) is tetrakis(diethylamino)phosphonium bromide.

5. A process according to claim 1 wherein the tetra (dihydrocarbylamino)phosphonium halide ingredient used in a) is tetrakis(diethylamino)phosphonium chloride.

6. A process according to claim 1 wherein said cyclic ether is tetrahydrofuran or a liquid alkyltetrahydrofuran, and wherein said non-solvent is a dialkyl ether having up to about 8 carbon atoms in the molecule.

7. A process according to claim 1 wherein said cyclic ether is tetrahydrofuran, and wherein said non-solvent is diethyl ether.

* * * * *